US007854231B1

(12) United States Patent
Mostad

(10) Patent No.: US 7,854,231 B1
(45) Date of Patent: Dec. 21, 2010

(54) ARM RETENTION SYSTEM FOR PHYSICAL THERAPY

(76) Inventor: Matt Mostad, 18281 58th Ave. Northeast, Kenmore, WA (US) 98028

( * ) Notice: Subject to any disclaimer, the term of this patent is extended or adjusted under 35 U.S.C. 154(b) by 123 days.

(21) Appl. No.: 11/974,924

(22) Filed: Oct. 15, 2007

Related U.S. Application Data

(60) Provisional application No. 60/829,500, filed on Oct. 13, 2006, provisional application No. 60/903,117, filed on Feb. 23, 2007.

(51) Int. Cl.
*A61B 19/00* (2006.01)
*E05B 75/00* (2006.01)

(52) U.S. Cl. .......................................... 128/869; 70/16

(58) Field of Classification Search ................. 128/869; 602/23, 20, 26, 27; 70/16; 428/121; 119/771
See application file for complete search history.

(56) References Cited

U.S. PATENT DOCUMENTS 1,823,697 A * 9/1931 Nenstiehl ....................... 70/16
1,899,092 A 2/1933 Hogan
2,319,390 A 5/1943 Dantolan
3,247,843 A 4/1966 Callahan
3,556,091 A 1/1971 Haig
3,970,316 A 7/1976 Westmoreland, Jr.
4,046,143 A * 9/1977 Bell ........................... 128/882
4,239,228 A 12/1980 Norman et al.
4,273,336 A 6/1981 Larkey
4,384,717 A 5/1983 Morris
4,693,241 A 9/1987 Trznadel
5,076,288 A 12/1991 Millard et al.
D352,572 S 11/1994 Pustizzi, Jr.
5,624,388 A * 4/1997 Lehr ........................... 602/20
D386,829 S 11/1997 Lovin
D417,318 S 11/1999 Lyons
5,996,380 A * 12/1999 Harris ........................... 70/16
6,073,631 A 6/2000 Wilhelmy
6,361,480 B1 3/2002 Coram
6,832,960 B2 12/2004 Thony
6,908,445 B2 6/2005 Watts
7,037,286 B1 5/2006 Reinhardt
7,166,760 B1 1/2007 Talbot
2005/0240132 A1 * 10/2005 Jones et al. ................... 602/19

* cited by examiner

*Primary Examiner*—Patricia M Bianco
*Assistant Examiner*—Ophelia Hawthorne
(74) *Attorney, Agent, or Firm*—Seed Intellectual Property Law Group PLLC

(57) ABSTRACT

Retention systems, methods, and components for controlling body movement are shown and described. Retention systems can be used to reduce, limit, or substantially eliminate unwanted body movement, such as arm movement. The disclosed systems can be quickly and conveniently positioned on a user's arm to keep the arms against or near the torso of the wear. The retention system can be worn when performing normal everyday activities.

22 Claims, 8 Drawing Sheets

ARM RETENTION SYSTEM FOR PHYSICAL THERAPY

CROSS-REFERENCES TO RELATED APPLICATIONS

This application claims the benefit under 35 U.S.C. §119 (e) of U.S. Provisional Patent Application No. 60/829,500 filed Oct. 13, 2006 and U.S. Provisional Patent Application No. 60/903,117 filed Feb. 23, 2007. These two provisional applications are incorporated herein by reference in their entireties.

BACKGROUND

1. Field

The present disclosure and disclosed embodiments generally relate to retention systems, and more specifically, to arm retention systems.

2. Description of the Related Art

Physical therapy programs often involve restricting movement of an injured body part. It may be important to limit the range of motion of an injured body part to prevent aggravation of the injury and to increase the rate of healing. Unfortunately, individuals often inadvertently move injured body parts outside the desired range of motion resulting in a significant increase in recovery time. Conventional rigid and soft braces or slings for limiting body motion may be extremely uncomfortable, especially when worn for a long period of time, leading patients to refrain from wearing the braces for the prescribed lengths of time. This may appreciably reduce the effectiveness of the therapy program.

Individuals, including injured and uninjured individuals, may have difficulty keeping their hands, arms, and other body parts away from other people or objects, especially when occupying a small or confined space. Unwanted body movements may be disruptive and embarrassing and, consequently, highly undesirable. For example, individuals traveling in transportation vehicles may want to limit their range of body movement because it may be difficult to keep their arms away from nearby passengers. In aircraft, for example, a passenger's arm may contact or fall into the lap of an adjacent passenger, even though an armrest is between the passengers. Unfortunately, armrests are unsuitable for limiting outward lateral arm movement, which may result in a violation of the personal space of the adjacent passenger and embarrassing situations. Overweight or obese individuals may have more difficulty in keeping their hands and arms away from other passengers.

BRIEF SUMMARY

Some embodiments disclosed herein include the realization that a retention system can position one or more body parts, such as an individual's arms, hands, fingers, legs, or feet, as well as other anatomical features. The retention system can receive and hold one or more body parts within in a desired range of motion or within a range of relative positions with respect to each other. The retention system may be used while sleeping, resting, sitting (e.g., sitting in tightly grouped seats), watching events (e.g., movies, theater, sporting events, etc.), traveling, and performing other everyday activities in a variety of settings. The retention system can also be incorporated into a various types of therapy programs or medical procedures.

In some embodiments, a retention system is configured to receive both hands of an individual. Once the wear's wrists are positioned in the retention system, the wearer can manipulate the retention system until it comfortably holds the wearer's arms. In some embodiments, the wearer can conveniently manipulate (e.g., twist) the retention system in order to tighten the retention system and to loosen the retention system for removal.

When the user is located in a somewhat confined space, the retention system can help reduce the likelihood of the user's hands and/or arms moving outside of a desired space. Such retention systems can keep the user's arm in proximity to the user's body when, for example, performing a wide range of activities (e.g., sleeping, sitting, resting, and the like).

In some embodiments, a restraining system comprises a first receiving portion having a first aperture configured to receive a right hand of a user, a second receiving portion having a second aperture configured to receive a left hand of the user, and a central section extending between the first and second receiving portions. The first receiving portion, second receiving portion, and central section are made of fabric (e.g., a strip of fabric) or other highly conformable material. The restraining system, in some embodiments, is an arm retention system for controlling relative movement between a pair of arms.

In some embodiments, an arm retention system for holding an individual's arms has a shape similar to the shape of the numeral 8. Other shapes are also possible. In some embodiments, at least one of first and second receiving loops of the arm retention system has a substantially circular shape, ovoid shape, and the like.

In some embodiments, a retention system includes a strip of material that defines two loops, each loop for surrounding a respective wrist. In some embodiments, the loops are the same size. In other embodiments, the loops are different sizes. A central section of the retention system includes sections of the strip that are coupled together.

In some embodiments, a one-piece retention system is made of a continuous strip of fabric. Separate pieces of material can be coupled together to form the continuous strip. Retention systems made of fabric can effectively restrain without utilizing complicated moving mechanical components.

In some embodiments, a method for retaining a user's arm is provided. The method includes wearing a first compliant, drapable loop of a retention system on the user's right arm. The retention system includes a wide, flat strip of fabric folded upon itself to define the first compliant, drapable loop and a second compliant, drapable loop opposing the first loop. The second loop is worn on the user's left arm, such that a central section of the retention system is positioned between the right arm and the left arm. The central section connects the first loop to the second loop. In some embodiments, the effective lengths of the first and second loops are reduced to tighten the first and second loops about the right and left arms. This tightening can be performed while a first length of a strip defining the first loop and a second length of a strip defining the second loop remain generally constant. Accordingly, the retention system can be tightened or loosened even though the loops have a fixed length.

In some embodiments, a method of positioning a user's right and left arm is provided. The method includes placing a soft, compliant retention system on the right arm and the left arm of the user. The retention system is worn on the right and left arms to secure the right and left arms together while the user is in a seat of a transportation vehicle. The retention system is adapted to be put on and removed by the user.

In some embodiments, a system for positioning a user's arms is provided. This system includes a strip of material folded upon itself. The strip includes a first drapable thin segment, a second drapable thin segment, and a central region. The first drapable thin segment has a first end, a second end, and a main body extended between the first and second ends. The second drapable thin segment has a first end, a second end, and a main body extending between the first and second ends of the second segment. The central region is connected to the first and second ends of the first segment and to the first and second ends of the second segment. The main bodies of the first and second segments form respective first and second receiving loops dimensioned and adapted to snugly surround the arms of the user to hold the user's hands near one another.

In yet other embodiments, a retention system for positioning arms of a user includes a first conformable strip, a second conformable strip, and a central junction. The first conformable strip defines a first wrist receiving loop. The second conformable strip defines a second wrist receiving loop. The central junction extends between and is coupled to the first strip and the second strip such that the central junction is interposed between the first and second openings of the first and second loops through which arms the user can be inserted.

DETAILED DESCRIPTION

The present detailed description is generally directed to retention systems configured to retain one or more body parts of a user. The body parts may be arms, hands, fingers, legs, ankles, feet, limbs, combinations thereof, and/or other anatomical features or appendages. Many specific details and certain representative embodiments are set forth in the following description and in FIGS. 1-15 to provide a thorough understanding of such embodiments. One skilled in the art, however, will understand that the disclosed embodiments may be practiced without one or more of the details described in the following description. As used herein, the term "arm" is broadly construed to include, without limitation, an upper limb of the human body. For example, the retention system may be applied to the limb extending from the shoulder to the hand. In various applications, retention systems can be worn about the wrists, forearms, or upper arms, even when performing different activities, including normal everyday activities. Additionally, various types of physical therapy programs can incorporate the use of the retention system to help patients.

It should also be noted that, as used in this specification and the appended claims, the singular forms "a," "an," and "the" include plural referents, unless the context clearly dictates otherwise. For example, the term "an opening" includes a single opening and/or a plurality of openings. The term "or" is generally employed in its sense including "and/or," unless the content clearly dictates otherwise. The terms "right" and "left" are used to describe the illustrated representative embodiments and are used consistently with the description of non-limiting exemplary applications. The terms right and left are used in reference to the user's body when the user is wearing the retention system, unless the context clearly indicates otherwise.

Figure 1:
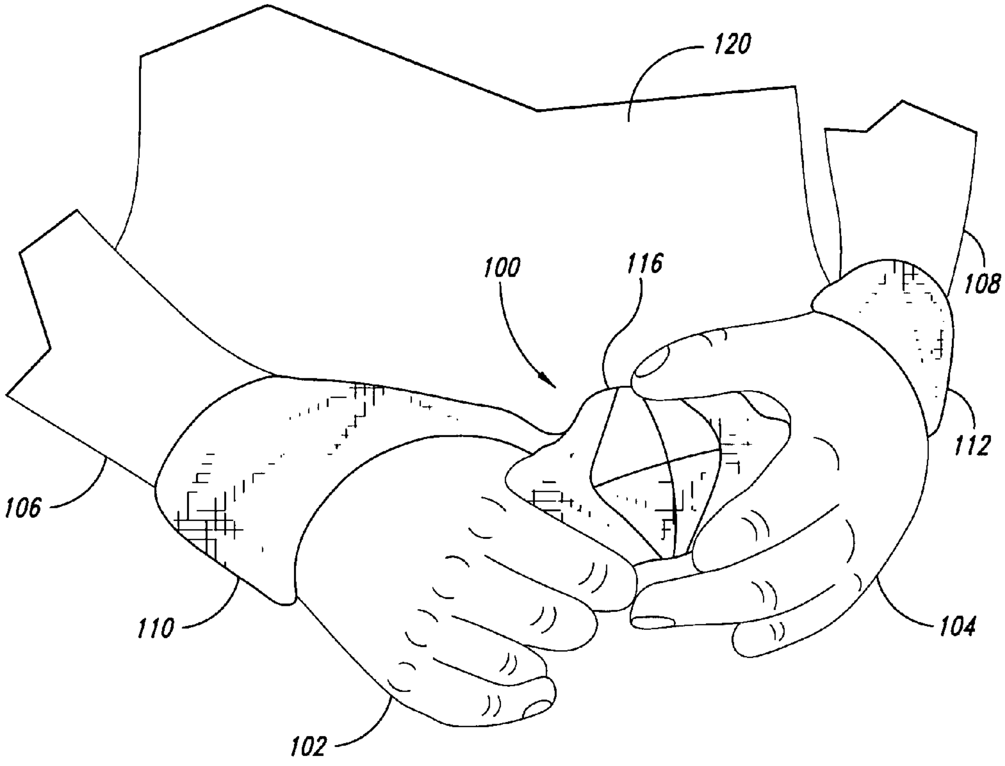
FIG. 1 is an isometric view of a retention system worn by a user, in accordance with one illustrated embodiment.

FIG. 1 illustrates a retention system 100 worn by a user. The retention system 100 is sized and dimensioned to receive an individual's right and left hands 102, 104 to locate the system 100 about the user's wrists. By holding the user's arms 106, 108 together, the retention system 100 reduces, limits, or substantially eliminates unwanted arm movement, thereby keeping the user's arms 106, 108 within a desired zone of movement to, for example, promote healing and prevent injuries during a physical therapy program. The retention system 100 can also be worn to improve body posture, as well as to prevent unwanted contact with nearby people or objects.

Figure 2:
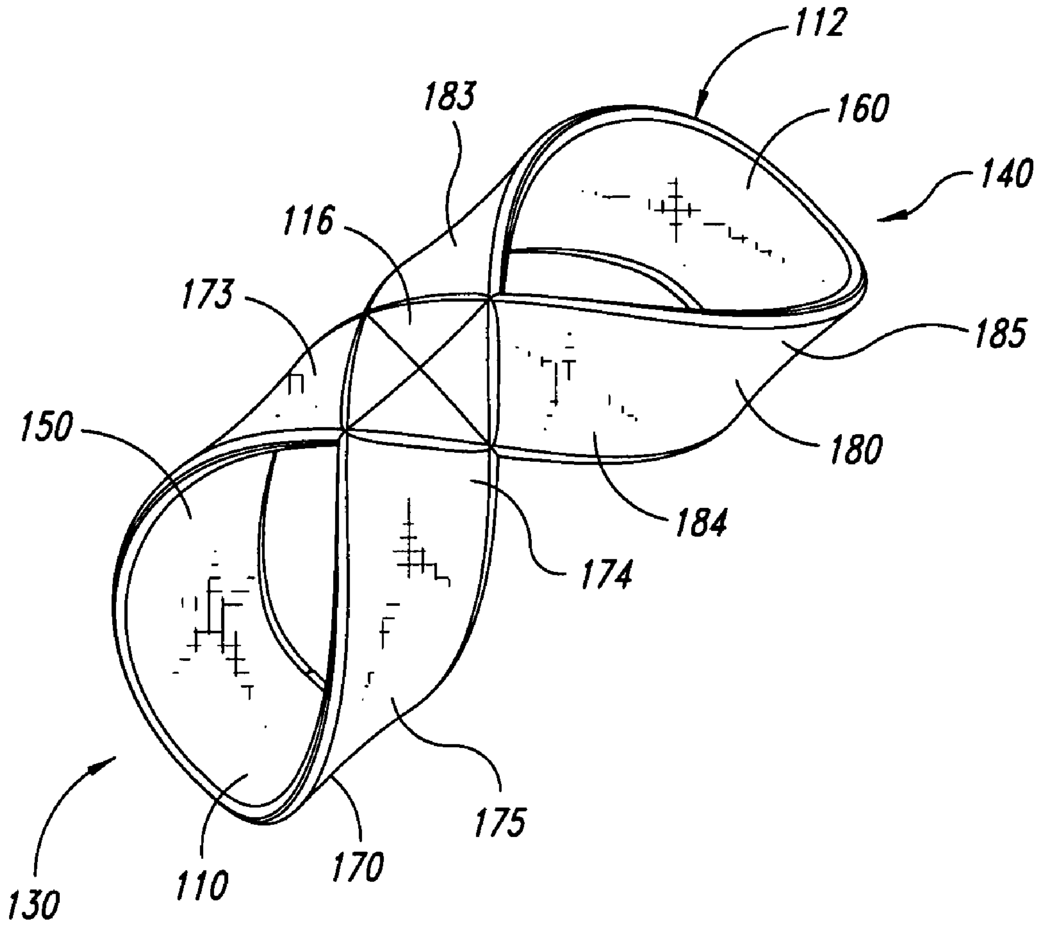
FIG. 2 is an isometric view of a retention system, in accordance with one illustrated embodiment.

The illustrated retention system 100 of FIGS. 1 and 2 includes a first loop 110 surrounding the right arm 106 and a second loop 112 surrounding the left arm 108. A central region 116, connected to the first and second loops 110, 112, is positioned generally between the right and left hands 102, 104. Such retention system 100 comfortably positions the user's unclasped or clasped right and left hands 102, 104 next to each other for a desired length of time, even prolonged lengths of time often associated with medical therapies, medical procedures, traveling, and the like. To provide a comfortable fit, the retention system 100 can be made, in whole or in part, of a highly conformable material that conforms closely to the user's skin to help distribute any applied pressure and to snugly grip the user's arms 106, 108. In contrast to metal handcuffs or other metal restraint devices, the retention system 100 can secure the user's hands close together without hurting the user, even if the user tries to separate their hands.

If the wearer is injured or prone to injuries attributable to body movements, the retention system 100 can significantly minimize or limit unwanted body movement that may lead to injuries. For example, if the user has an injured right shoulder that may be aggravated by excessive arm movement, the retention system 100 can pull the arm 106 against the user's torso 120 to reduce or limit shoulder movement, thereby preventing any aggravation. Because the retention system 100 comfortably surrounds and grips the user's wrists, it can be worn for extended periods of time while the user performs a wide range of normal everyday activities, such as watching entertainment (e.g., live theater, movies, opera), sporting events (e.g., baseball games), traveling, sleeping, sitting, and the like.

Referring to FIG. 2, a first conformable strip 130 defines the first loop 110 for receiving the right arm 106, and a second conformable strip 140 defines the second loop 112 for receiving the left arm 108. The first and second strips 130, 140 define apertures 150, 160, respectively, and can be generally similar to each other and, accordingly, the following description of one of the strips applies equally to the other, unless indicated otherwise.

The first strip 130 includes a flexible first drapable segment 170 having a first end 173, a second end 174, and a continuous main body 175 extending between the first and second ends 173, 174. The second strip 140 includes a flexible second drapable segment 180 having a first end 183, a second end 184, and a continuous main body 185 extending between the first and second ends 183, 184. The central region 116 shown in FIGS. 2 and 3 is connected to and interposed between both first ends 173, 183 and second ends 174, 184.

The illustrated first and second strips 130, 140 are made of a flexible material (e.g., plastic, polymers, natural fibers, synthetic fibers, leather, and the like). In some embodiments, the strips 130, 140 are made, in whole or in part, of fabric. As used herein, the term "fabric" is broadly construed to include, but is not limited to, cloth or cloth-like material made by weaving, knitting, and/or felting fibers. Cotton, polyester, blends (e.g., cotton polyester blends), silk, and the like are suitable materials for form the strips 130, 140, and/or the entire retention system 100. Retention systems 100 made mostly or entirely of fabric can be soft and very lightweight.

In some embodiments, each of the first and second strips 130, 140 is made of a drapable fabric or other material suitable for hanging or resting limply, or both. Drapable fabrics are especially well suited for comfortably securing body parts without causing an appreciable amount of trauma. As such, the strips 130, 140 made of a drapable fabric may be sufficiently flexible to conform closely about the user's arms 106, 108 under a wide range of body positions. A strip can be, without limitation, a single continuous and uninterrupted strip, a plurality of segmented strips physically coupled together (either directly or indirectly), or other type of feature for looping about a wearer's arm. Additionally, strips disclosed herein can be monolayer or multilayer strips with a uniform width (see FIGS. 2 and 3) or non-uniform width.

Figure 3:
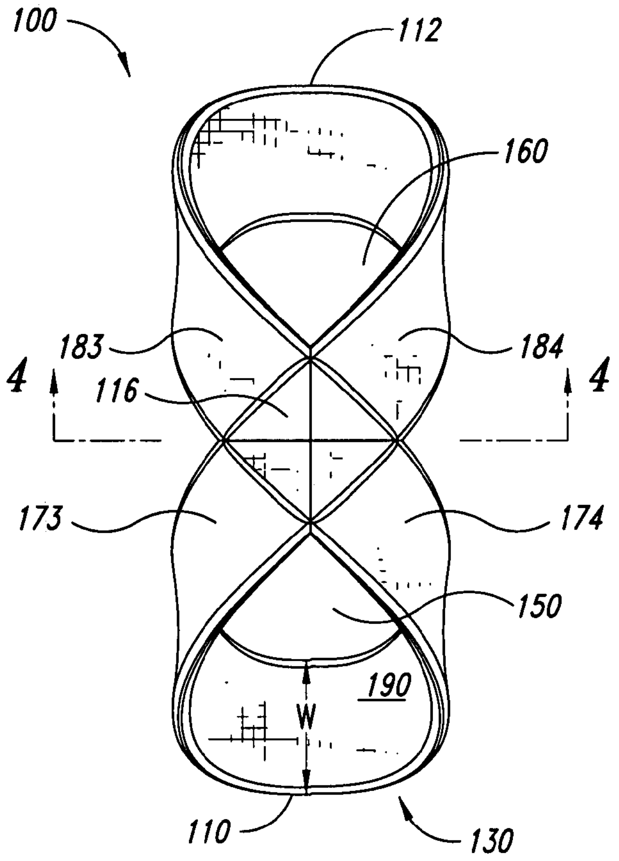
FIG. 3 is a top view of the retention system of FIG. 2.
Figure 4:
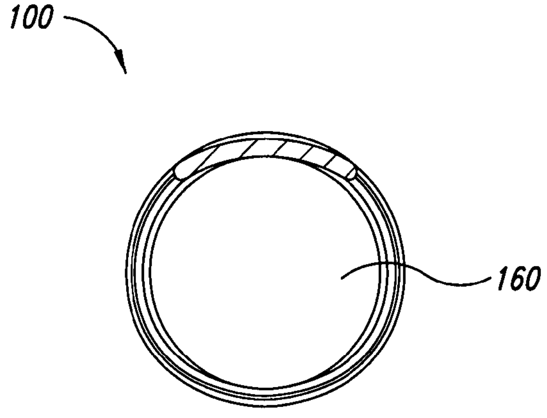
FIG. 4 is a cross-sectional view of the retention system of FIG. 3 along line 4-4, in accordance with one illustrated embodiment.
Figure 5:
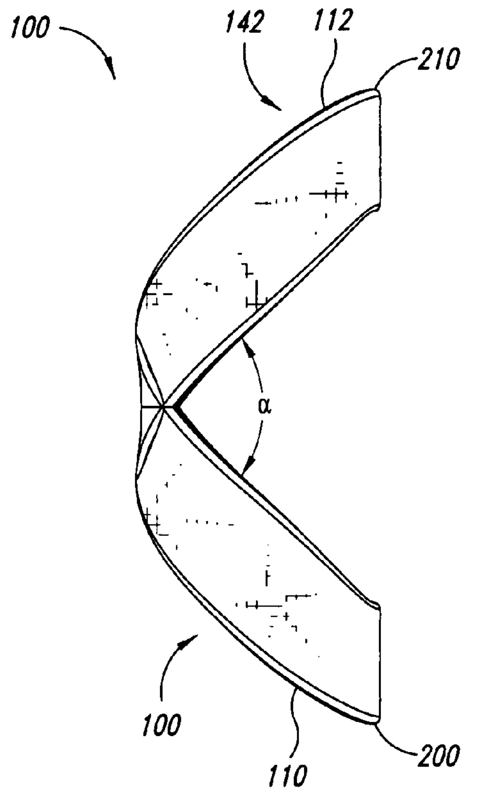
FIG. 5 is a side elevational view of the retention system of FIG. 2.
Figure 6:
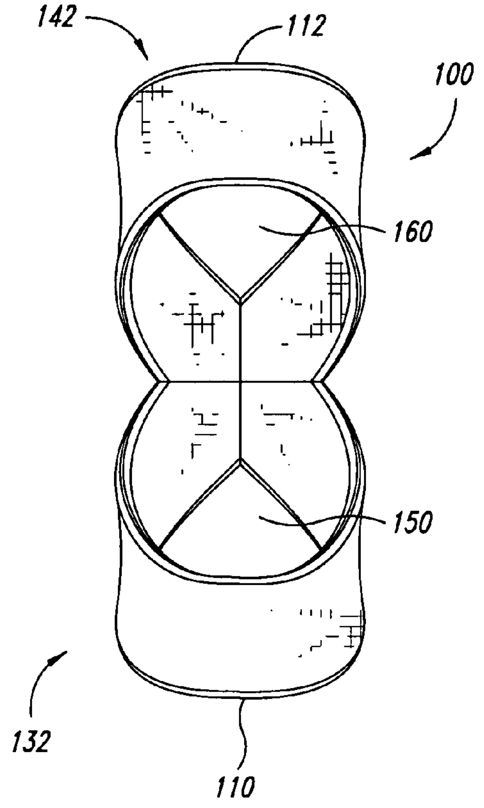
FIG. 6 is a bottom view of the retention system of FIG. 2.
Figure 7:
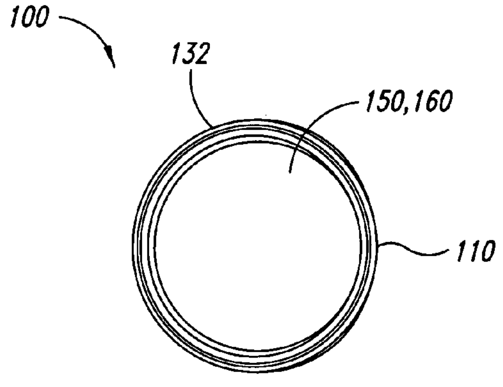
FIG. 7 is a front elevational view of the retention system of FIG. 2.
Figure 8:
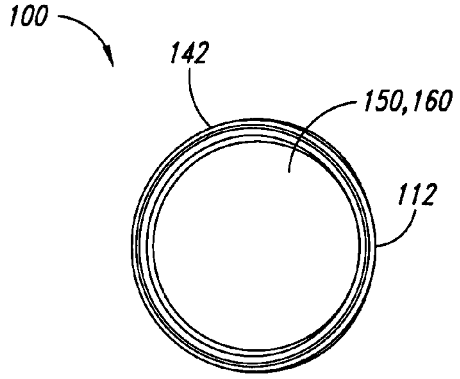
FIG. 8 is a back elevational view of the retention system of FIG. 2.

Referring to FIG. 3, the strip 130 has an average width W selected for desired level of comfort. For example, the width W can be equal to or greater than about 0.25 inch such that a face 190 for contacting the user is sufficiently large to prevent friction burns, bruising, and other types of injuries often associated with traditional restraint devices. In some embodiments, the width W is equal to or greater than about 0.5 inch. Such embodiments are especially well suited for extended use when sitting down. In some embodiments, the width W is equal to or greater than 1 inches. Such embodiments are especially well suited for use while sleeping. In some embodiments, the width W is equal to or greater than 1.5 inches or 2 inches. Such embodiments are especially well suited for use while traveling in transportation vehicles in which the user is subjected to rapid accelerations. The width W can be selected based on the user's physical condition and environmental settings.

The sizes of the apertures 150, 160 can be selected to achieve the desired fit. In some embodiments, each of the apertures 150, 160 is substantially larger than the user's hands such that the user's hands can be conveniently inserted into the first and second loops 110, 112. The first and second loops 110, 112 may then fit loosely about the user's arms. If the apertures 150, 160 are openings that are slightly larger than the user's hands, the loops 110, 112 may closely surround around the user's arm even before adjusting the effective lengths of the loops 110, 112, as discussed below.

Referring to FIGS. 5 to 8, the first and second loops 110, 112 can be angled with respect to each other when worn and can define the apertures 150, 160 having complementary shapes as the arms 106, 108. Outmost portions 200, 210 of the first and second loops 110, 112 are at opposing outermost ends of the retention system 100. The illustrated first and second loops 110, 112 define an angle $\alpha$ in the range of about 70 degrees to about 120 degrees. Other angles are also possible based on the desired interaction with the user's body. If the retention system 100 is made of a compliant material, it can be bent, folded, twisted, or otherwise manipulated.

Figure 9:
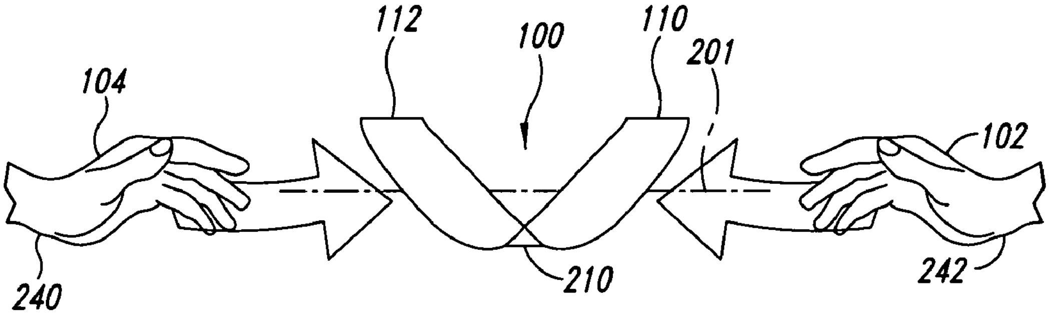
FIG. 9 shows a pair of hands being inserted into a pair of opposing loops of a retention system, in accordance with one illustrated embodiment.
Figure 10:
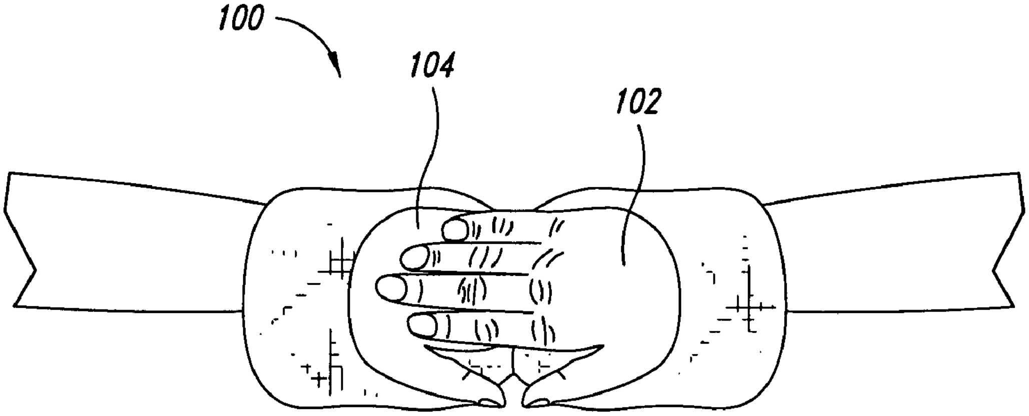
FIG. 10 shows the retention system of FIG. 9 surrounding the wear's wrists.

To wear the retention system 100, the right and left hands 102, 104 can be sequentially or simultaneously inserted into the respective first and second loops 110, 112. As shown in FIGS. 9 and 10, which are from the perspective of the wearer, the right hand 102 can be moved inwardly through the aperture of the first loop 110. Likewise, the left hand 104 can be inserted through the aperture of the second loop 112. The hands 102, 104 can be moved through the respective first and second loops 110, 112 until the retention system 100 surrounds both wrists 240, 242, as shown in FIG. 10.

Before or after adjusting the fit of the retention system 100, the user's arms 106, 108 can be brought towards one another such that the retention system 100 is oriented somewhat transverse to one or both of the user's arms. In this manner, the right and left arms 106, 108 are secured together and relative movement between them is thus reduced or limited.

Figure 11:
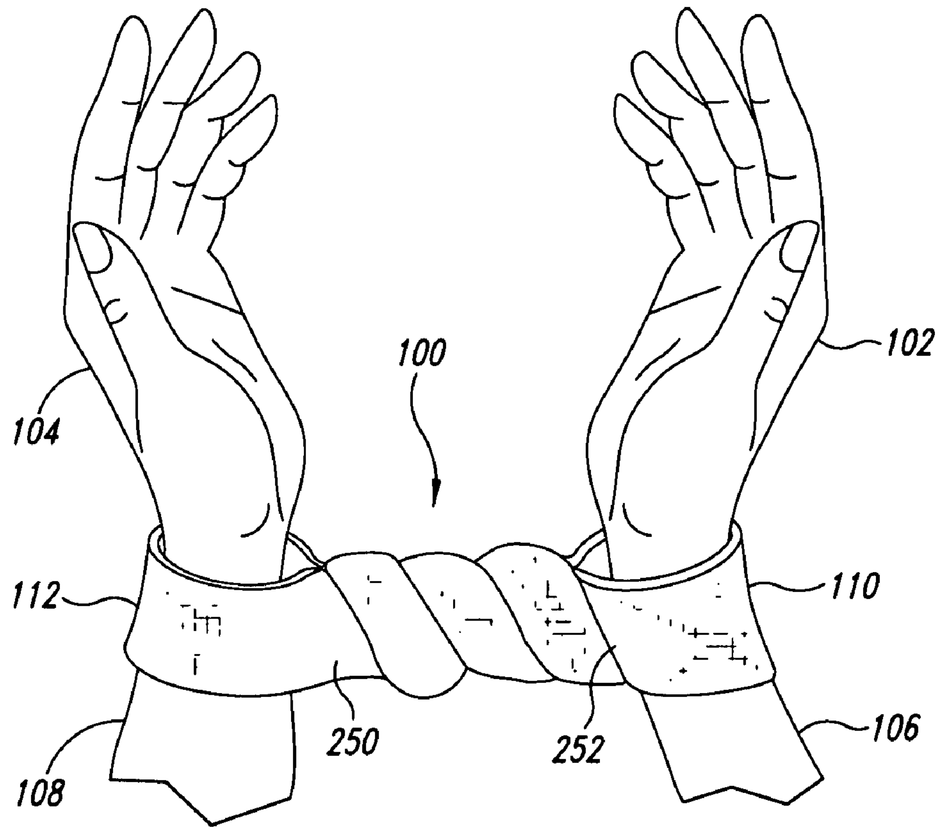
FIG. 11 shows the retention system of FIG. 9 after a central section of the retention system has been twisted.

In some embodiments, including the illustrated embodiment of FIGS. 9 to 11, to tighten the retention system 100, the user can rotate one of the hands 102, 104 (preferably the hand is angled outwardly from an axis 201 of FIG. 9) about the axis 201 while the other hand 102, 104 and both arms remain generally stationary. In this manner, the retention system 100 can be twisted to reduce the size of one or both of the apertures 150, 160. FIG. 11 shows the central region 116 and inner portions of both loops 106, 108 twisted to squeeze the arms 106, 108. The number of revolutions around the axis 201 can be increased or decreased to increase or decrease the tension in each of the first and the second loops 110, 112. Other means for tensioning the retention system 100 can also be used.

As shown in FIG. 11, the effective length of the loops 110, 112 can be reduced because the inner portions 250, 252 of the loops 110, 112 are also twisted, even though the length of the material forming the loops 110, 112 does not change. One or both of the first and second loops 110, 112 may thus be twisted to draw (e.g., constrict) the loops 110, 112 about the arms 106, 108 to achieve the desired fit. In some embodiments, most of the portion of the retention system 100 between the arms 106, 108 is twisted.

When the retention system 100 is worn, the user's hands 102, 104 and arms 106, 108 are kept in proximity to the user's upper body 120, as shown in FIG. 1. In some embodiments, the retention system 100 and the hands 102, 104 can rest in the user's lap while the user rests or sleeps. In this manner, the user's arms 106, 108 can be held closely to the user's body for a desired length of time.

To remove the retention system 100, the retention system 100 can be untwisted to allow the user to withdraw the arms 106, 108 from the untwisted retention system 100. The retention system 100 can then be folded up and reused any number at times, or discarded.

Figure 12:
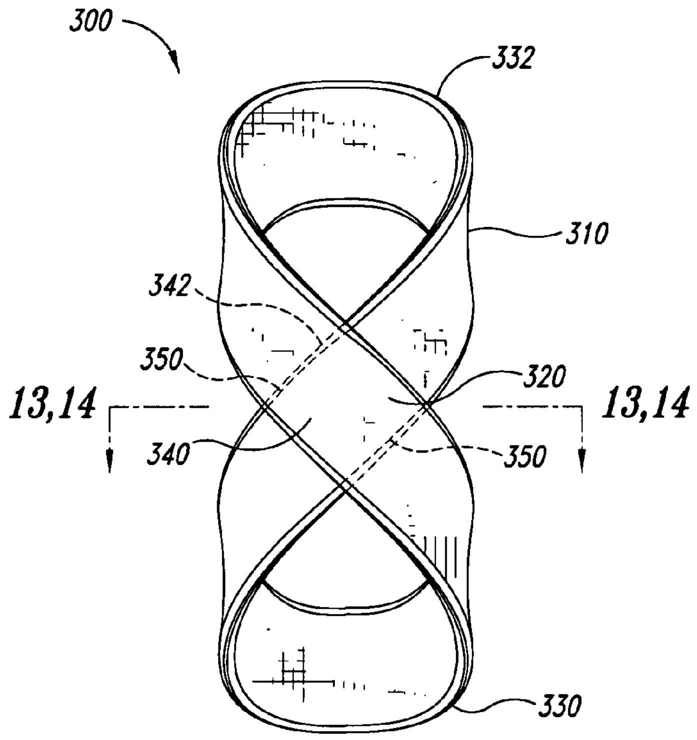
FIG. 12 is a top view of a one-piece retention system, in accordance with one illustrated embodiment.
Figure 13:
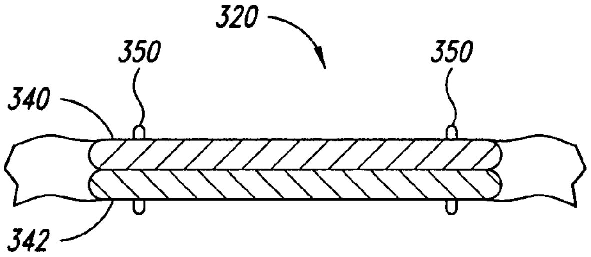
FIG. 13 is a cross-sectional view of the retention system of FIG. 12 taken along line 13-13, in accordance with one illustrated embodiment.

FIG. 12 shows a retention system 300 that includes a continuous and uninterrupted strip 310 folded upon itself to form a figure-eight configuration, as viewed from above. A central region 320 is a junction between first and second loops 330, 332 and can include a pair of mated sections 340, 342. Stitching or other coupling features can permanently or temporarily couple the mated sections 340, 342 together. In the illustrated embodiment of FIGS. 12 and 13, stitching 350 (shown in phantom in FIG. 12) permanently couples the crisscrossed sections 340, 342 together.

Figure 14:
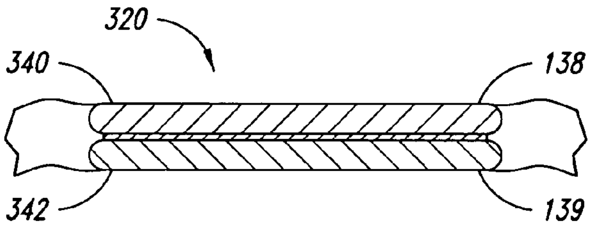
FIG. 14 is a cross-sectional view of the retention system of FIG. 12 taken along line 14-14, in accordance with another illustrated embodiment.

FIG. 14 illustrates the central region 320 including hook and loop type fastener assemblies. The upper section 340 can include a hook fastener assembly that is removably coupled to a loop fastener assembly of the lower section 342 such that the sections 340, 342 can be quickly and conveniently coupled together and separated. Other types of coupling features (e.g., snaps, buttons, magnets, adhesives, and the like) can be used to couple the sections 340, 342 together. If the sections 340, 342 do not have coupling features, the central region 320 can be twisted to prevent unwanted separation or to adjust the tension of the loops 330, 332, or both.

The retention systems described herein can be used in a wide range of applications, such as physical therapy programs (discussed above), medical procedures, traveling, and the like. The retention systems can treat at least one of a physical disability (e.g., permanent physical impairments attributable to trauma, diseases, and birth defects), physical malfunction (e.g., torn muscles), and pain of the user, as well as other conditions treated using physical therapy. To perform medical procedures, including, but not limited to, surgical procedures (e.g., open surgical procedures such as open heart surgery, semi-open procedures, and the like), minimally invasive procedures, medical tests, and the like, the retention system 100 can be worn to prevent the patient's arms and hands from interfering with the physician, falling from a surgical table, and the like. The wearer may be a patient under anesthesia, including general anesthesia or sedation. After performing the medical procedure, the retention system 100 can be removed and discarded or reused. If the retention system 100 is reused, it can be sterilized between each use.

The retention systems can be worn by a user in various types of vehicles. As used herein, the term "vehicle" is a broad term that includes, but is not limited to, aircraft (e.g., airplanes such as commercial transport planes, helicopters, and the like), automobiles (e.g., trucks, sports utility vehicles, cars, and the like), and other transportation vehicles used to transport humans. For example, the retention system can be worn by an individual occupying an airplane seat. The user's hands, held by the retention system, can be positioned in front of the user's body while sitting in the seat for at least 10 minutes, 20 minutes, or 1 hour. Wearing the retention system for at least 10 minutes can provide enough time for the user to reach a state of relaxation without focusing on actively positioning their arms. Because airplane seats may be relatively small, the retention system can limit body movement to help prevent unwanted body contact with any occupants in adjacent seats. The retention system thus serves to ensure that proper personal space is maintained. For example, adjacent passengers often inadvertently contact each other if they both use the armrest between them. To prevent this type of contact, which may be socially uncomfortable, the retention system can urge the user's hands and/or arms away from the armrest and, in some embodiments, in a close proximity to the body.

Figure 15:
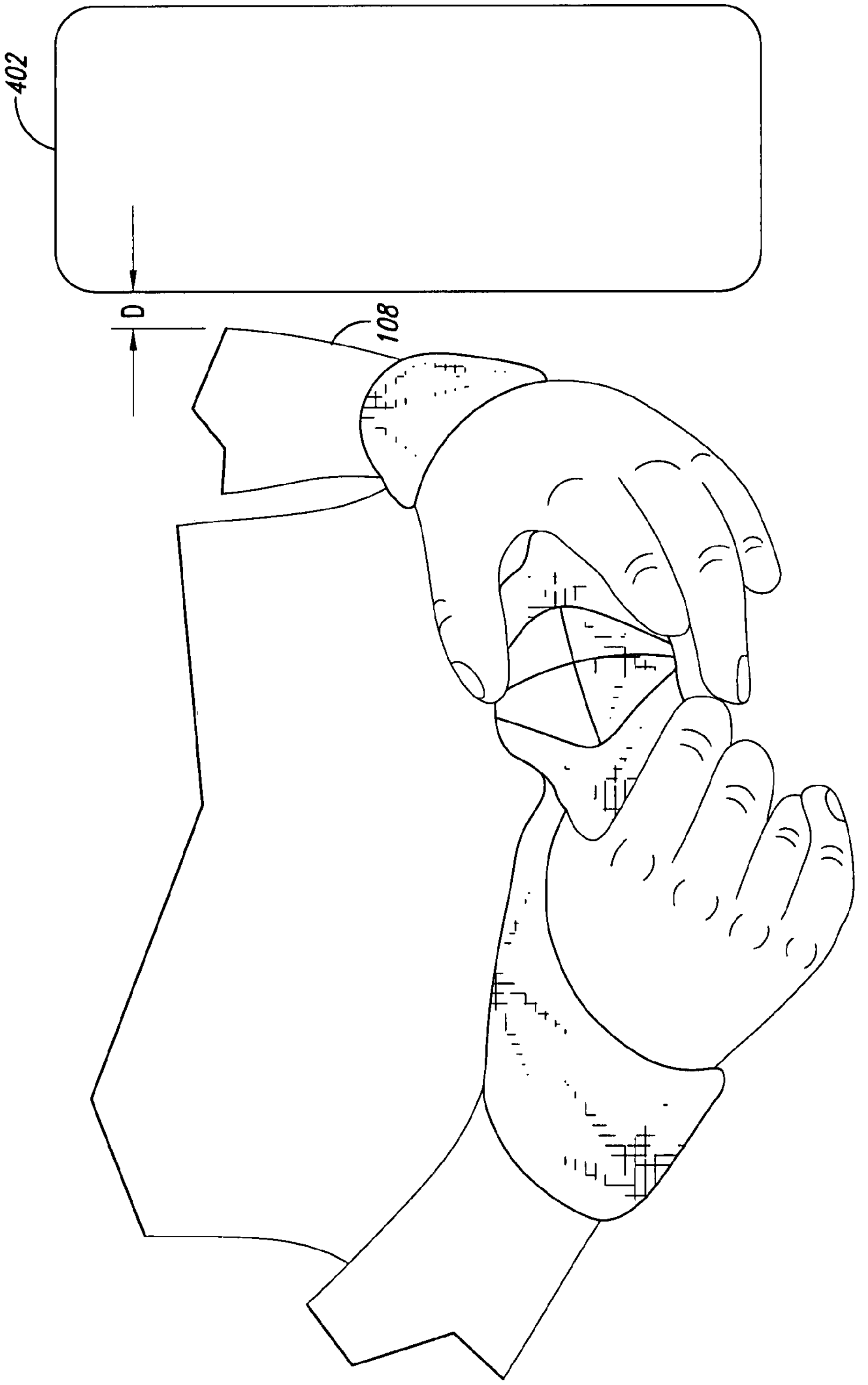
FIG. 15 shows a user wearing a retention system that holds the user's arm away from an armrest, in accordance with one illustrated embodiment.

In some embodiments, the user's arm is held at least a distance D (e.g., 1 inch, 1.5 inches, or 2 inches) from the armrest 402, as shown in FIG. 15. To further reduce the risk of unwanted body contact, the user's arms can pulled inwardly against the user's body such that the distance D is equal to or greater than 3 inches. The desired arm position may vary based on the size of the user. For example, arms of a heavy or obese individual may have to be pulled snugly against the torso to keep the arms spaced from the armrest 402.

Various methods and techniques described above provide a number of ways to carry out the invention. Of course, it is to be understood that not necessarily all objectives or advantages described may be achieved in accordance with any particular embodiment described herein. Thus, for example, those skilled in the art will recognize that the methods may be performed in a manner that achieves or optimizes one advantage or group of advantages as taught herein without necessarily achieving other objectives or advantages as may be taught or suggested herein.

Furthermore, the skilled artisan will recognize the interchangeability of various features from different embodiments disclosed herein. Similarly, the various features and acts discussed above, as well as other known equivalents for each such feature or act, can be mixed and matched by one of ordinary skill in this art to perform methods in accordance with principles described herein. Additionally, the methods which are described and illustrated herein are not limited to the exact sequence of acts described, nor are they necessarily limited to the practice of all of the acts set forth. Other sequences of events or acts, or less than all of the events, or simultaneous occurrence of the events, may be utilized in practicing the embodiments of the invention.

The embodiments, features, systems, devices, materials, methods and techniques described herein may, in some embodiments, be similar to any one or more of the embodiments, features, systems, devices, materials, methods and techniques described in U.S. Provisional Patent Application No. 60/829,500 filed Oct. 13, 2006 and U.S. Provisional Patent Application No. 60/903,117 filed Feb. 23, 2007, which are incorporated herein by reference in their entireties. In addition, the embodiments, features, systems, devices, materials, methods and techniques described herein may, in certain embodiments, be applied to or used in connection with any one or more of the embodiments, features, systems, devices, materials, methods and techniques disclosed in the above-mentioned U.S. Provisional Patent Application No. 60/829,500 filed Oct. 13, 2006 and U.S. Provisional Patent Application No. 60/903,117 filed Feb. 23, 2007.

Although the invention has been disclosed in the context of certain embodiments and examples, it will be understood by those skilled in the art that the invention extends beyond the specifically disclosed embodiments to other alternative embodiments and/or uses and obvious modifications and equivalents thereof. Accordingly, it is not intended that the invention be limited, except as by the disclosed embodiments and the appended claims.

What is claimed is:

1. A method for retaining a user's arms, the method comprising:

wearing a first compliant, drapable loop of a retention system on the user's right arm, the retention system including a wide flat strip of fabric folded upon itself to define the first compliant, drapable loop and a second compliant, drapable loop opposing the first loop;

wearing the second loop of the retention system on the user's left arm such that a central section of the retention system is positioned between the right arm and the left arm, the central section connects the first loop to the second loop;

holding the left arm and the right arm against the user's torso using the retention system while the user occupies a seat; and allowing the left arm and the right arm to move together away from the user's torso while the retention system, the left arm, and the right arm are not coupled to any stationary structure.

2. The method of claim 1, wherein the user occupies the seat of a transportation vehicle while the first and second loops are worn on the right and left arms.

3. The method of claim 2, wherein the transportation vehicle is an airplane or automobile.

4. The method of claim 1, further comprising:

reducing effective lengths of the first and second loops to tighten the first and second loops about the right and left arms, respectively, while a first length of the strip defining the first loop and a second length of the strip defining the second loop remain constant.

5. The method of claim 1, further comprising:

inserting a right hand and a left hand of the user through first and second openings of the first and second loops, respectively, such that the first and second loops hang loosely on the right arm and left arm, respectively; and after inserting the right and left hands through the first and second openings, tightening the first and second loops about the right and left arms, respectively, by twisting inner portions of the first and second loops;

wherein the first loop and the second loop of the retention system are worn after tightening the first and second loops about the right and left arms, respectively.

6. The method of claim 1, further comprising:

adjusting sizes of the first and second loops by twisting the central section of the retention system by moving the right hand relative to the left hand.

7. The method of claim 1, further comprising:

treating at least one of a physical disability, a physical malfunction, and pain of the user associated with the right arm or left arm by holding the left arm and right arm against the user's torso.

8. The method of claim 1, further comprising:

performing a medical procedure on the user while the first and second loops are worn on the right and left arms such that the right and left arms are proximate the user's torso.

9. The method of claim 1, further comprising:

positioning the user's right and left hands in front of the user while the user is in the seat for at least 10 minutes.

10. A method of positioning a user's right arm and left arm, the method comprising:

placing a soft, compliant retention system on the right arm and the left arm of the user;

wearing the retention system on the right and left arms to secure the right and left arms together, the retention system adapted to be put on and removed by the user;

holding the left arm and the right arm using the retention system; and allowing the left arm and the right arm to move together away from the user's torso while the retention system, the left arm, and the right arm are not coupled to any stationary structure.

11. The method of claim 10, further comprising:

tightening the retention system about the right and left arms by constricting a first loop of the retention system about the right arm and a second loop of the retention system about the left arm.

12. The method of claim 10, further comprising:

adjusting effective lengths of a first loop of the retention system and a second loop of the retention system, while the retention system is worn, by manually manipulating the retention system without changing lengths of sections of the retention system forming the first and second loops.

13. The method of claim 10, further comprising:

tightening the retention system about the right and left arms by twisting most of the retention system extending between the right and left arms.

14. The method of claim 10, wherein the user wears the compliant retention system while in a seat of an aircraft that is flying.

15. The method of claim 10, wherein wearing the retention system further includes:

surrounding the right arm with a first flexible strip of the retention system, the first strip having a first end, a second end, and a main body extending between the first and second ends;

surrounding the left arm with a second flexible strip of the retention system, the second strip having a first end, a second end, and a main body extending between the first and second ends of the second strip; and positioning a central region of the retention system between the right and left arms, the central region is connected to the first and second ends of the first strip and the first and second ends of the second strip, wherein the main bodies of the first and second strips form respective first and second receiving loops that snugly surround the right and left arms of the user.

16. The method of claim 10, further comprising:

sitting in a seat of a transportation vehicle while first and second loops of the retention system are worn on the right and left arms, respectively.

17. The method of claim 10, further comprising:

performing a medical procedure on the user while the left arm and the right arm are held against the user's torso using the retention system.

18. A method for retaining a user's arms while the user occupies a seat, the method comprising:

wearing a first compliant, drapable loop of a retention system on the user's right arm, the retention system including the first compliant, drapable loop and a second compliant, drapable loop;

wearing the second compliant, drapable loop on the user's left arm; and limiting movement of the user's left arm with respect to the right arm using the retention system while the retention system extends across the user's body and is freely movable with respect to the seat and while the user is not coupled to any stationary structure.

19. The method of claim 18, wherein limiting movement of the user's left arm with respect to the right arm comprises allowing the left arm and the right arm to move together with a full range of normal motion.

20. The method of claim 18, further comprising:

pulling the left arm and the right arm against the user's torso using the retention system while the user occupies the seat.

21. The method of claim 18, further comprising:

holding the user's right hand and left hand in the user's lap without connecting the user and without connecting the retention system to any stationary structure.

22. The method of claim 18, further comprising:

reducing effective lengths of the first compliant, drapable loop and the second compliant, drapable loop to move the user's right arm away from a right arm rest and to move the user's left arm away from a left arm rest.

* * * * *